United States Patent [19]

Pretzer et al.

[11] 4,331,560

[45] May 25, 1982

[54] CATALYST AND PROCESS FOR PREPARING ORGANIC ISOCYANATES

[75] Inventors: Wayne R. Pretzer, Gibsonia; Richard B. Pannell, Allison Park, both of Pa.

[73] Assignee: Gulf Research & Development Company, Pittsburgh, Pa.

[21] Appl. No.: 255,693

[22] Filed: Apr. 20, 1981

[51] Int. Cl.³ ..................... B01J 31/02; C07C 118/06
[52] U.S. Cl. .............................. 252/429 R; 252/430; 260/453 PC
[58] Field of Search ............. 260/453 PC; 252/429 R, 252/430

[56] References Cited

U.S. PATENT DOCUMENTS

| | | | |
|---|---|---|---|
| 3,576,835 | 4/1971 | Smith et al. | 260/453 PC |
| 3,674,827 | 7/1972 | Rao et al. | 260/453 PC |
| 4,267,070 | 5/1981 | Nefedov et al. | 252/429 R |

*Primary Examiner*—Dolph H. Torrence
*Attorney, Agent, or Firm*—Deane E. Keith; Forrest D. Stine; Joseph J. Carducci

[57] ABSTRACT

Organic isocyanates are prepared by reacting an organic nitrocompound with carbon monoxide in the presence of a novel catalyst system. The catalyst system is comprised of a noble metal compound, a heteroaromatic nitrogen compound, and an oxide of thorium or uranium.

11 Claims, No Drawings

CATALYST AND PROCESS FOR PREPARING ORGANIC ISOCYANATES

CROSS REFERENCE TO RELATED PATENTS

The subject matter of this application is related to that of U.S. patent application Ser. No. 255,695 filed concurrently with this application.

BACKGROUND

This invention relates to a novel catalytic system useful in the conversion of organic nitro compounds to the corresponding organic isocyanates.

Organic isocyanates are used extensively in the preparation of urethane foams, fibers and coatings. Organic isocyanates also find use in the production of surface active agents, biocides, and the like.

Organic isocyanates have been prepared commercially from organic nitro compounds by a process which involves conversion of the nitro compounds to the corresponding amines and thereafter reacting the amines with phosgene. A newer and more efficient process permits the preparation of organic isocyanates directly from organic nitro compounds through a reaction with carbon monoxide at elevated temperatures and pressures in the presence of a catalyst. Appropriate catalyst systems that have been proposed have included noble metals, Lewis acids, and combinations thereof. A catalyst system comprised of a noble metal halide, a heteroaromatic nitrogen compound, and an component selected from the oxides of vanadium, molybdenum, tungsten, niobium, chromium and tantalum is disclosed in U.S. Pat. No. 3,576,835. In U.S. Pat. No. 3,674,827, it is suggested that further improvement in the recovery of organic isocyanates through use of such a catalyst system may be effected by the addition of discrete particles of iron oxide to the catalyst system.

SUMMARY OF THE INVENTION

The present inventors have discovered that catalyst systems useful in the preparation of organic isocyanates from organic nitro compounds, and specifically those comprising mixtures of a noble metal or a noble metal compound and a heteroaromatic nitrogen compound, are greatly improved in yield and selectivity to isocyanate, in the reaction of the carbon monoxide with the organic nitro compounds, through the addition to the system of an oxide of thorium or uranium.

Accordingly, the present invention provides an improvement in the process for preparing organic isocyanates, particularly aromatic isocyanates, by reacting the appropriate organic nitro compound with carbon monoxide at suitable elevated temperature and pressure in the presence of noble metal-based catalyst systems. The improvement comprises employing as the catalyst a system containing (1) a noble metal compound selected from the group consisting of noble metals, compounds containing noble metals and complexes of noble metals with one or more organic or inorganic compounds; (2) one or more heteroaromatic nitrogen compounds, the aromatic ring thereof containing
  (a) five or six members,
  (b) only nitrogen and carbon,
  (c) no more than two nitrogen atoms, and
  (d) at least two double bonds; and
(3) an actinide oxide selected from the oxides of uranium and thorium, as hereinafter defined.

The present invention also provides a novel catalyst useful in the preparation of organic isocyanates. The catalyst system is comprised of (1) a noble metal compound selected from the group consisting of noble metals, compounds containing noble metals and complexes of noble metals with one or more organic or inorganic compounds; (2) one or more heteroaromatic nitrogen compounds, the aromatic ring thereof containing
  (a) five or six members,
  (b) only nitrogen and carbon,
  (c) no more than two nitrogen atoms, and
  (d) at least two double bonds, and
(3) an actinide oxide selected from the oxides of uranium and thorium.

DETAILED DESCRIPTION OF THE INVENTION AND PREFERRED EMBODIMENTS

The Isocyanate Preparation Process

The subject invention provides a novel catalyst system useful in the direct conversion of organic nitro compounds to the corresponding organic isocyanates by reaction of the organic nitro compound with carbon monoxide at elevated temperatures and pressures. The term "organic nitro compound" should be understood to indicate any organic compound containing one or more nitro groups which are capable of being converted to isocyanate groups through the catalyzed reaction with carbon monoxide. Any organic nitro compound capable of being converted to an organic isocyanate may be employed. Thus, where the term "organic nitro compound" is used throughout this disclosure and claims, it is intended that the term define substituted and unsubstituted aromatic, cycloaliphatic, and aliphatic mono- or poly- nitro compounds which can be reacted to form the corresponding mono- or poly- isocyanates by means of the catalytic process described herein. A list of suitable organic nitro compounds is set forth in the disclosure of U.S. Pat. No. 3,576,835, and such disclosure is hereby incorporated by reference. It should be pointed out that isomers and homologues of the aforesaid organic nitro compounds, as well as mixtures of one or more such organic nitro compounds, may be employed. Additionally, compounds which have both nitro and isocyanate substituents, e.g., 2-iso-cyanato-4-nitrotoluene, may also be employed as a reactant in the process, the only limitation being that the organic nitro compound be capable of being converted to the corresponding organic isocyanate.

The process of this invention is particularly effective in the conversion of aromatic nitro compounds to the corresponding aromatic isocyanates. Aromatic nitro compounds, as the term is used in the description and claims hereof, will refer to aromatic compounds such as benzene, naphthalene and the like having at least one nitro group attached directly to an aromatic hydrocarbon nucleus. As indicated earlier the aromatic hydrocarbon nucleus may also be substituted. Preferred aromatic nitro compounds suitable to be used in the practice of this invention include the nitro-benzenes, both mono- and poly- nitro, including isomeric mixtures thereof, nitro-alkylbenzenes, including the various nitrated toluenes and nitrated xylenes, nitrated biphenyl and nitrated diphenyl methylene. Among others preferred are bis (nitro-phenoxy) alkylene and bis (nitrophenoxy) alkyl ethers.

Generally, the organic nitro compound will contain from about one to about twenty carbon atoms. The preferred aromatic nitro compounds will be those in which the nitro group or groups appear on benzene or naphthalene rings, and will have between about six and about fourteen carbon atoms.

The Catalyst System

The catalyst system of this invention will be a mixture or a complex containing three critical components:
(1) a noble metal compounds,
(2) a heteroaromatic nitrogen compound, and
(3) an oxide of uranium and thorium.

The Noble Metal Compound

The first component of the catalyst system of the invention is a noble metal compound. The noble metals include gold, iridium, osmium, palladium, platinum, rhenium, rhodium, ruthenium, and silver. Compounds of these elements which may be used in accordance with this process include oxides, sulfates, nitrates, halides, carbonates, sulfides, acetates, oxylates, other organic salts, carbonyls, organic complexes, and the like. The term "noble metal compound" shall refer to both the elemental form of the noble metal and to compounds of the noble metal throughout the description and claims. The preferred noble metal compounds are selected from the group consisting of the noble metals, noble metal halides, noble metal oxides, organic salts of noble metals and organic complexes of noble metals. It is especially preferred that the noble metal be one of the platinum series, including palladium, rhodium, platinum, iridium and mixtures thereof. The most preferred noble metal compounds are the halides of palladium and rhodium, specifically palladous dichloride and rhodium trichloride.

THE HETEROAROMATIC NITROGEN COMPOUND

The heteroaromatic nitrogen compound component of the catalyst is a compound having between five and six members in the ring, only carbon and nitrogen in the ring, no more than two nitrogen atoms in the ring, and having at least two double bonds in the ring. Derivatives of such heteroaromatic nitrogen compounds may also be used. Throughout the description and claims, the term derivative when used in conjunction with heteroaromatic nitrogen compounds includes additions to the parent heteroaromatic nitrogen containing ring. Representative heteroaromatic nitrogen compounds and derivatives thereof which are suitable for use as components of the catalyst of this invention are listed below. A more exhaustive listing of suitable heteroaromatic compounds may be found in U.S. Pat. No. 3,576,835, which is hereby incorporated by reference.
(1) 1-methyl pyrrole
(2) imidazole
(3) carbazole
(4) pyridine
(5) 2,6-dimethyl pyridine
(6) 2,4,6-trimethyl pyridine
(7) 4-phenyl pyridine
(8) quinoline
(9) isoquinoline
(10) benzo isoquinoline
(11) pyrazine
(12) cinnoline
(13) pyridine hydrochloride
(14) laurylpyridium chloride
(15) picolinic acid
(16) 4-picoline-1-oxide
(17) 3-picoline-1-oxide
(18) pyridine.$SO_3$
(19) (pyridine)$_3$ $FeCl_3$
(20) Pd (isoquinoline)$_2$ $Cl_2$ The preferred heteroaromatic nitrogen compounds are those selected from the group consisting of pyridine, isoquinoline, quinoline, and derivatives thereof. It is also preferred to utilize the heteroaromatic nitrogen compound in the catalyst system of the invention in the form of a complex with a noble metal halide of component one. The complex may be preformed prior to its addition to the reaction mixture as described in U.S. Pat. No. 3,576,835, which is hereby incorporated by reference. Alternatively, the catalyst components may be added separately to the reaction mixture and the complex formed in situ. The preferred complexes are those formed by combining the preferred noble metal halides with the preferred heteroaromatic nitrogen, specifically Pd (pyridine)$_2$ $Cl_2$, Pd (pyridine)$_2$ $Cl_4$, Pd (isoquinoline)$_2$ $Cl_4$, Pd (isoquinoline)$_2$ $Cl_2$, Rh (pyridine)$_3$ $Cl_3$ and Rh (isoquinoline)$_3$ $Cl_3$.

The Actinide Oxide

While organic isocyanates may be produced with a catalyst comprised of a noble metal or a noble metal compound and a heteroaromatic nitrogen compound, the selectivity and yield to isocyanates is greatly increased by the addition of a third component to the catalyst system. This third component is selected from the oxides of the actinide group of heavy metals, in particular, the oxides of uranium and thorium. It appears the oxides of uranium and thorium are the only actinide compounds practical for use in the present invention due to the fact that the other members of this group are highly radioactive and rapidly decay to produce compounds which do not possess the useful properties required in this invention.

Additionally, it appears that all oxides of the two actinides within the scope of the present invention are not suitable. With regard to uranium oxides, it has been established that both $U_2O_5$ and $U_3O_8$ are acceptable. The red form of $UO_3$, obtained by dehydrating $UO_3$.$H_2O$ on the other hand, appears to contribute little or no improvement in selectivity and yield to isocyanates when used as a component of the invention catalyst system. While this may be due to the structural dissimilarity from $U_2O_5$, this is probably not a complete answer, due to the fact that $ThO_2$ is a suitable oxide for the catalyst systems, but is structurally different from $U_2O_5$.

Process and System Parameters

Certain constituents of each of the three mentioned elements of the catalyst system are significantly more effective than others in improving the selectivity and yield to isocyanates of the process. The halides, oxides, acetates, and organic complexes of the noble metals are among the more effective noble metal compounds. Among the more effective heteroaromatic nitrogen compounds are:
(1) pyridine
(2) 2,6-dimethyl pyridine
(3) 2,4,6-trimethyl pyridine
(4) 4-phenyl pyridine
(5) 3-chloro pyridine (6) lauryl pyridium chloride
(7) quinoline
(8) 7,8-benzo quinoline
(9) 2-chloro quinoline
(10) isoquinoline
(11) benzo isoquinoline
(12) imidazole
(13) picolinic acid
(14) 4-picoline-1-oxide
(15) 3-picoline-1-oxide Pyridine, quinoline and isoquinoline are particularly preferred heteroaromatic nitrogen compounds.

The preferred actinide oxides are those of uranium and thorium. More particularly the preferred compounds are $U_2O_5$, $U_3O_8$ and $ThO_2$. The surface area of the heavy metal oxide should be in the range from about 0.05 $m^2$/gm to about 30 $m^2$/gm. Preferably the minimum surface area should not be less than 0.1 $m^2$/gm. The maximum surface area will be limited by practical restraints of obtaining the particle size. Surface areas in the range of 2 $m^2$/gm are currently commercially available.

The catalyst system can be self-supported or deposited on a support or carrier. Alumina, asbestos, barium sulfate, calcium carbonate, carbon, diatomaceous earth, fuller's earth and analogous materials are useful as carriers for this purpose.

The noble metal compounds, the heteroaromatic nitrogen compound, and the heavy metal compound may be added separately to the organic nitro compound reactant or if desired may be premixed prior to adding to the organic nitro compound.

The proportion of the catalyst system is generally equivalent to between about 0.001 and about 500 percent, and preferably between about 1.0 and about 100 percent by weight of the organic nitro compound. Greater or lesser proportions may be used.

The molar ratio of the heteroaromatic compound to noble metal compound is generally between about 0.1:1 and about 20:1 and preferably between about 0.5:1 and 10:1.

The weight ratio of the noble metal compound component of the catalyst system to the actinide oxide component of the catalyst system is generally between 0.001:1 and 50:1 and preferably in the range between of about 0.05:1 and 25:1.

Although the process of this invention operates effectively in the absence of solvent, overall improved yields can be obtained through the use of a solvent chemically inert to the reactants and catalyst. Among suitable solvents are aliphatic, cycloaliphatic, and aromatic hydrocarbons such as heptane, cyclohexane, toluene, xylene and halogenated aliphatic and aromatic hydrocarbons such as dichloromethane, tetrachloroethane, trichlorotrifluoroethane, monochloronaphthalene, monochlorobenzene, dichlorobenzene, trichlorobenzene, and perchloroethylene. The choice of solvent for the production of a particular isocyanate will be dependent upon such considerations as the solubility of the organic nitro compound feed, the solubility of the resulting organic isocyanate, and the technique to be used for isolation of the organic isocyanate.

The proportion of solvent is not critical and any proportion maybe used. Generally the weight percent of the organic nitro compound in the solvent is between 5.0 and 75.0 percent.

The order of mixing of the reactants and the catalyst components is not critical and may be varied as desired.

A typical embodiment utilizing a batch process entails charging the organic nitro compound, solvent, the noble metal compound, the heteroaromatic nitrogen compound and the actinide oxide into the reactor. The reactor is then pressured with carbon monoxide and heated to the desired temperature. Additional carbon monoxide is fed to the reactor as needed. The preferred reaction pressure is between 100 and 20,000 p.s.i.g., but greater or lesser pressures may be employed. The reaction temperature is generally maintained above 25° C. and preferably between about 100° and about 250° C.

Reaction time is dependent upon starting materials, catalyst concentration, temperature and pressure, as well as the configuration of the processing equipment. In a batch process, reaction times of one-half hour to twenty hours are usually required to obtain the desired degree of reaction. After the reaction is completed, the temperature of the reactor may be lowered to ambient temperature, the pressure is vented, and the reaction products removed. The catalyst is then removed from the reaction products by filtration, centrifugation, or other suitable solid-liquid separation techniques. The organic isocyanate is then isolated from the reaction product by fractional distillation. Extraction, sublimation and other suitable techniques may be used instead of distillation to separate the organic isocyanate from the unreacted organic nitro compound and from any by products formed.

The reaction can also be carried continously. In a continuous process, the reaction time may be substantially instantaneous and residence time in the reactor much shorter than in a batch process. An example of such a continuous process would be to slurry the catalyst system with the organic nitro compound feed and a suitable solvent; introduce the feed-catalyst slurry into a continuous reactor of such configuration as would provide the required temperature, pressure, and residence time; simultaneously introduce the carbon monoxide; after passage of the reaction mixture through the reactor, separate the resulting isocyanate from the reaction mixture; and recycle the catalyst, any unreacted starting materials, and the solvent.

The organic isocyanates produced by this process are suitable for the production of polyurethane compositions such as foams, coatings, fibers, and the like by reacting the organic isocyanate with an appropriate polyether polyol in the presence of a suitable catalyst and if desired in the presence of a foaming agent. The organic isocyanates may be utilized in the preparation of other useful compositions such as biologically active compounds.

The following examples are presented to describe the present invention in more detail. Such examples are presented for purposes of illustration only and shall not under any circumstances be deemed as limiting the present invention.

EXAMPLES 1–17

Into a 300 cc. stainless steel autoclave, orthodichlorobenzene (solvent), the organic nitro compound, and the catalyst consisting of a noble metal compound, a heteroaromatic nitrogen compound, and an additional metal compound, if used, were charged. The $ThO_2$ if used had a surface area of 1.4 $m^2$/gm. The autoclave was sealed, purged with nitrogen and then pressured with carbon monoxide to a pressure of about 1000 p.s.i.g., which is lower than the desired reaction pressure. The autoclave was then heated to the desired temperature and the pressure was adjusted to the desired value. A constant pressure was maintained throughout the reaction by constantly admitting carbon monoxide into the reactor on demand from a high pressure reservoir. After the desired reaction period, the autoclave was cooled and the reaction product removed. The product was weighed and analyzed by vapor phase chromatography. The reactants, catalyst, conditions and results are tabulated in Table I.

EXAMPLES 18-28

The general procedure of Examples 1-17 was repeated. The $U_2O_5$ if used had a surface area 0.24 $m^2$/gm. The reactants, catalyst, conditions, and results are tabulated in Table II.

TABLE I

| Example No. | Noble Metal Compound (Gms) | Heteroaromatic Compound (Mls) | Additional Catalyst Component (Gms) | Organic Nitro Compound Feed, (Gms) | Solvent (Ml) | Temp, °C. | Time, Hrs | CO Pressure, #/In² (MPa) | Per Cent Conversion | Per Cent Selectivity to Isocyanates | Mols Isocyanates Produced Per Mol of Palladium Per Hour |
|---|---|---|---|---|---|---|---|---|---|---|---|
| 1 | $PdCl_2$ (0.5) | Pyridine (1.0) | $ThO_2$ (0.1) | 2,4-dinitrotoluene (10) | 45 | 175 | 1.5 | 3500 (24.1) | 100 | 68 | 8.83 |
| 2 | $PdCl_2$ (0.5) | Pyridine (1.0) | $ThO_2$ (0.1) | 2,4-dinitrotoluene (10) | 45 | 150 | 1.5 | 3500 (24.1) | 34 | 97 | 4.65 |
| 3 | $PdCl_2$ (0.5) | Pyridine (1.0) | $ThO_2$ (0.1) | 2,4-dinitrotoluene (10) | 45 | 160 | 1.5 | 3500 (24.1) | 49 | 89 | 5.66 |
| 4 | $PdCl_2$ (0.5) | Pyridine (1.0) | $ThO_2$ (0.1) | 2,4-dinitrotoluene (10) | 45 | 175 | 1.5 | 2000 (13.8) | 46 | 90 | 5.38 |
| 5 | $PdCl_2$ (0.5) | Pyridine (1.0) | $ThO_2$ (0.1) | 2,4-dinitrotoluene (10) | 45 | 175 | 1.5 | 2500 (17.2) | 56 | 73 | 5.31 |
| 6 | $PdCl_2$ (0.5) | Pyridine (1.0) | $ThO_2$ (0.1) | 2,4-dinitrotoluene (10) | 45 | 175 | 1.5 | 3000 (20.7) | 75 | 94 | 9.16 |
| 7 | $PdCl_2$ (1.08) | Pyridine (0.93) | $Fe_2O_3$ (0.91) | 2,4-dinitrotoluene (18) | 45 | 200 | 4.0 | 4000 (27.6) | 100 | 31 | 1.26 |
| 8 | $PdCl_2$ (0.50) | Pyridine (0.50) | $Fe_2O_3$ (0.503) | 2,4-dinitrotoluene (9) | 45 | 175 | 3.0 | 3500 (24.1) | 66 | 26 | 1.0 |
| 9 | $PdCl_2$ (0.50) | Quinoline (0.71) | $Fe_2O_3$ (0.50) | 2,4-dinitrotoluene (9.03) | 45 | 175 | 3.0 | 3500 (24.1) | 10 | 19 | 0.11 |
| 10 | $PdCl_2$ (0.50) | Acetonitrile (0.30) | $Fe_2O_3$ (0.50) | 2,4-dinitrotoluene (9) | 45 | 175 | 3.0 | 3600 (24.8) | 100 | 30 | 1.75 |
| 11 | $PdCl_2$ (0.502) | Pyridine (0.50) | $MoO_3$ (0.513) | 2,4-dinitrotoluene (9) | 45 | 200 | 3.0 | 3500 (24.1) | 100 | 49 | 2.85 |
| 12 | Palladium Acetate (0.76) | Pyridine (0.81) | $ThO_2$ (0.08) | 2,4-dinitrotoluene (10) | 45 | 175 | 3.0 | 3500 (24.1) | 96 | 99 | 6.96 |
| 13 | $PdCl_2$ (0.25) | Pyridine (0.25) | None | Nitrobenzene (6.02) | 90 | 175 | 2 | 3500 (24.1) | 31 | 100 | 5.38 |
| 14 | $PdCl_2$ (0.51) | Pyridine (0.50) | $Fe_2O_3$ (0.50) | Nitrobenzene (19.2) | 80 | 175 | 3 | 3500 (24.1) | 42 | 45 | 3.41 |
| 15 | $PdCl_2$ (0.25) | Pyridine (0.50) | None | Nitrobenzene (12.0) | 50 | 200 | 2 | 3500 (24.1) | 19 | 81 | 5.35 |
| 16 | $PdCl_2$ (0.50) | Pyridine (1.0) | $ThO_2$ (0.1) | Nitrobenzene (12.0) | 45 | 175 | 2 | 3500 (24.1) | 54 | 83 | 7.77 |
| 17 | $PdCl_2$ (0.50) | Pyridine (0.51) | $Th(NO_3)_4$ (0.1) | Nitrobenzene (10) | 34.5 | 175 | 4 | 3500 (24.1) | 90 | 55 | 3.55 |

TABLE II

| Example No. | Noble Metal Compound (Gms) | Heteroaromatic Compound (Ml) | Additional Catalyst Component (Gms) | Organic Nitro Compound Feed, (Gms) | Solvent (Ml) | Temp, °C. | Time, Hrs | CO Pressure, #/In² (MPa) | Per Cent Conversion | Per Cent Selectivity to Isocyanates | Yield |
|---|---|---|---|---|---|---|---|---|---|---|---|
| 18 | $PdCl_2$ (0.25) | Pyridine (0.25) | None | Nitrobenzene (6.02) | 90 | 175 | 2 | 3500 (24.1) | 31 | 99 | 30.7 |
| 19 | $PdCl_2$ (0.25) | Pyridine (0.50) | None | Nitrobenzene (12.04) | 50 | 200 | 2 | 3500 (24.1) | 19 | 81 | 15.4 |
| 20 | $PdCl_2$ (0.51) | Pyridine (0.50) | $Fe_2O_3$ (0.5) | Nitrobenzene (19.26) | 80 | 175 | 3 | 3500 (24.1) | 42 | 45 | 18.9 |
| 21 | $PdCl_2$ (1.08) | Pyridine (0.93) | $Fe_2O_3$ (0.91) | 2,4-dinitrotoluene (18.01) | 45 | 200 | 4 | 4000 (27.6) | 100 | 31 | 31.0 |
| 22 | $PdCl_2$ (0.50) | Pyridine (0.50) | $Fe_2O_3$ (0.503) | 2,4-dinitrotoluene (9.00) | 45 | 175 | 3 | 3500 (24.1) | 66 | 26 | 17.2 |
| 23 | $PdCl_2$ (0.50) | Quinoline (0.71) | $Fe_2O_3$ (0.50) | 2,4-dinitrotoluene (9.03) | 45 | 175 | 3 | 3500 (24.1) | 10 | 19 | 1.9 |
| 24 | $PdCl_2$ (0.50) | Acetonitrile (0.30) | $Fe_2O_3$ (0.50) | 2,4-dinitrotoluene (9.00) | 45 | 175 | 3 | 3600 (24.8) | 100 | 30 | 30.0 |
| 25 | $PdCl_2$ (0.502) | Pyridine (0.50) | $MoO_3$ (0.513) | 2,4-dinitrotoluene (9.00) | 45 | 200 | 3 | 3500 (24.1) | 100 | 49 | 49.0 |

TABLE II-continued

| Example No. | Noble Metal Compound (Gms) | Heteroaromatic Compound (Ml) | Additional Catalyst Component (Gms) | Organic Nitro Compound Feed, (Gms) | Solvent (Ml) | Temp, °C. | Time, Hrs | CO Pressure, #/In² (MPa) | Per Cent Conversion | Per Cent Selectivity to Isocyanates | Yield |
|---|---|---|---|---|---|---|---|---|---|---|---|
| 26 | PdCl₂ (0.506) | Pyridine (0.50) | V₂O₅ (0.50) | 2,4-dinitrotoluene (9.00) | 45 | 200 | 3 | 3500 (24.1) | 100 | 75 | 75.0 |
| 27 | PdCl₂ (0.50) | Pyridine (0.51) | U₂O₅ (0.10) | Nitrobenzene (10.0) | 34.5 | 175 | 4 | 3500 (24.1) | 98 | 99 | 97.0 |
| 28 | PdCl₂ (0.50) | Pyridine (1.02) | U₂O₅ (0.10) | 2,4-dinitrotoluene (10.0) | 45 | 175 | 4 | 3500 (24.1) | 80 | 99 | 79.2 |
| 29 | PdCl₂ (0.50) | Pyridine (1.02) | UO₃ (0.10) | 2,4-dinitrotoluene (10) | 45 | 175 | 4 | 3500 (24.1) | 1 | 99 | 9.0 |

The foregoing description has been directed to a particular embodiment of the invention for the purposes of illustration and explanation. Those skilled in the art will readily appreciate modifications and changes in the procedures set forth without departing from the scope and spirit of the invention. Applicants' intent is that the following claims be interpreted to embrace all such modifications and variations.

The subject matter which applicants claim as their invention is:

1. A process for preparing an organic isocyanate, which comprises:
   reacting an organic nitro compound with carbon monoxide in the presence of a catalyst comprised of
   (a) a noble metal compound,
   (b) a heteroaromatic nitrogen compound having a ring with
      (1) between five and six members in the ring,
      (2) only nitrogen and carbon in the ring,
      (3) no more than two nitrogens in the ring, and
      (4) containing at least two double bonds in the ring,
   wherein the molar ratio of the heteroaromatic nitrogen compound to the nobel metal compound lies between about 0.1 to 1 and 20 to 1,
   (c) an actinide oxide selected from the oxides of uranium and thorium, wherein the weight ratio of the noble metal compound to the actinide oxide lies between about 0.001 to 1 and 50 to 1.

2. The process of claim 1, wherein said noble metal compound is selected from the group consisting of noble metals, noble metal halides, noble metal oxides, organic salts of noble metals and organic complexes of noble metals.

3. The process of claim 2, wherein the heteroaromatic nitrogen compound is selected from the group consisting of
   (a) pyridine
   (b) 2,6-dimethyl pyridine
   (c) 2,4,6-trimethyl pyridine
   (d) 4-phenyl pyridine
   (e) 3-chloro pyridine
   (f) lauryl pyridium chloride
   (g) quinoline
   (h) 7,8 benzo quinoline
   (i) 2-chloro quinoline
   (j) isoquinoline
   (k) benzo isoquinoline
   (l) imidazole
   (m) picolinic acid
   (n) 4-picoline-1-oxide
   (o) 3-picoline-1-oxide 4. A process for preparing an aromatic isocyanate, which comprises:
   reacting an aromatic nitro compound with carbon monoxide in the presence of a catalyst comprised of
   (a) a noble metal compound,
   (b) a heteroaromatic nitrogen compound having a ring with
      (1) between five and six members in the ring,
      (2) only nitrogen and carbon in the ring,
      (3) no more than two nitrogens in the ring, and
      (4) at least two double bonds in the ring,
   wherein the molar ratio of the heteroaromatic nitrogen compound to the noble metal compound lies between about 0.1 to 1 and 20 to 1,
   (c) an actinide oxide selected from the oxides of uranium or thorium, wherein the weight ratio of the noble metal compound to the actinide oxide lies between about 0.001 to 1 and 50 to 1.

5. The process of claim 4, wherein the said noble metal compound is selected from the group consisting of noble metals, noble metal halides, noble metal oxides, organic salts of noble metals and organic complexes of noble metals.

6. The process of claim 5, wherein the said heteroaromatic compound is selected from the group consisting of
   (a) pyridine
   (b) 2,6-dimethyl pyridine
   (c) 2,4,6-trimethyl pyridine
   (d) 4-phenyl pyridine
   (e) 3-chloro pyridine
   (f) lauryl pyridium chloride
   (g) quinoline
   (h) 7,8 benzo quinoline
   (i) 2-chloro quinoline
   (j) isoquinoline
   (k) benzo isoquinoline
   (l) imidazole
   (m) picolinic acid
   (n) 4-picoline-1-oxide
   (o) 3-picoline-1-oxide 7. A process for preparing an aromatic, isocyanate which comprises:
   reacting an aromatic nitro compound with carbon monoxide in the presence of
   (a) a noble metal chloride selected from the group consisting of the chlorides of palladium and rhodium, (b) a heteroaromatic nitrogen compound selected from the group consisting of pyridine, quinoline, and isoquinoline, (c) an actinide oxide selected from the group consisting of $U_2O_5$, $U_3O_8$, and $ThO_2$, wherein the molar ratio of the heteroaromatic nitrogen compound to the noble metal compound lies between about 0.5 to 1 and 10 to 1 and the weight ratio of the noble metal compound to the actinide oxide lies between about 0.05 to 1 and 25 to 1.

8. A catalyst system useful in the preparation of organic isocyanates from the corresponding organic nitro compounds, which comprises in combination:
   (a) a noble metal compound,
   (b) a heteroaromatic nitrogen compound having a ring with,
      (1) between five and six members in the ring,
      (2) only nitrogen and carbon in the ring,
      (3) no more than two nitrogens in the ring,
      (4) at least two double bonds in the ring,
   wherein the molar ratio of the heteroaromatic nitrogen compound to the noble metal compound lies between about 0.1 to 1 and 20 to 1,
   (c) an actinide oxide selected from the group consisting of $U_2O_5$, $U_3O_8$ and $ThO_2$, wherein the weight ratio of the noble metal compound to the actinide oxide lies between about 0.001 to 1 and 50 to 1.

9. A catalyst system as in claim 8 wherein, the said noble metal compound is selected from the group consisting of noble metals, noble metal halides, noble metal oxides, organic salts of noble metals and organic complexes of noble metals.

10. A catalyst system as in claim 9 wherein, the said heteroaromatic nitrogen compound is selected from the group consisting of
    (a) pyridine
    (b) 2,6-dimethyl pyridine
    (c) 2,4,6-trimethyl pyridine
    (d) 4-phenyl pyridine
    (e) 3-chloro pyridine
    (f) lauryl pyridium chloride
    (g) quinoline
    (h) 7,8 benzo quinoline
    (i) 2-chloro quinoline
    (j) isoquinoline
    (k) benzo isoquinoline
    (l) imidazole
    (m) picolinic acid
    (n) 4-picoline-1-oxide
    (o) 3-picoline-1-oxide 11. A catalyst system useful in the preparation of aromatic isocyanates from the corresponding aromatic nitro compound, which comprises in combination:
    (a) a noble metal chloride selected from the group consisting of the chlorides of palladium and rhodium,
    (b) a heteroaromatic nitrogen compound selected from the group consisting of pyridine, quinoline, and isoquinoline,
    (c) an actinide oxide selected from the group consisting of $U_2O_5$, $U_3O_8$, and $ThO_2$,
wherein the molar ratio of the heteroaromatic nitrogen compound to the noble metal compound lies between about 0.5 to 1 and 10 to 1 and the weight ratio of the noble metal compound to the actinide oxide lies between about 0.05 to 1 and 25 to 1.

* * * * *